(12) United States Patent
Hearn

(10) Patent No.: US 8,876,824 B2
(45) Date of Patent: Nov. 4, 2014

(54) STERNUM FIXATION DEVICE

(75) Inventor: James P. Hearn, West Chester, PA (US)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

(21) Appl. No.: 13/540,924

(22) Filed: Jul. 3, 2012

(65) Prior Publication Data

US 2012/0271311 A1  Oct. 25, 2012

Related U.S. Application Data

(60) Continuation of application No. 11/030,507, filed on Jan. 5, 2005, now Pat. No. 8,221,421, which is a division of application No. 10/073,133, filed on Feb. 13, 2002, now Pat. No. 6,872,210.

(60) Provisional application No. 60/270,620, filed on Feb. 23, 2001.

(51) Int. Cl.
*A61B 17/80* (2006.01)
*A61B 17/82* (2006.01)
*A61B 17/86* (2006.01)

(52) U.S. Cl.
CPC ......... *A61B 17/8009* (2013.01); *A61B 17/8076* (2013.01); *A61B 17/8057* (2013.01); *A61B 17/8085* (2013.01); *A61B 17/823* (2013.01); *A61B 17/863* (2013.01); *Y10S 606/905* (2013.01)
USPC ............................................. 606/71; 606/905

(58) Field of Classification Search
USPC ........................ 606/70, 71, 280–299, 905, 60, 606/246–279, 300–331
See application file for complete search history.

(56) References Cited

U.S. PATENT DOCUMENTS

| | | | |
|---|---|---|---|
| 408,080 | A | 7/1889 | Carroll |
| 2,254,620 | A | 9/1941 | Miller |
| 2,472,009 | A | 5/1949 | Gardner |
| 2,486,303 | A | 10/1949 | Longfellow |
| 2,669,747 | A | 2/1954 | Detaranto |
| 3,068,869 | A | 12/1962 | Shelden et al. |

(Continued)

FOREIGN PATENT DOCUMENTS

| | | |
|---|---|---|
| CA | 2439094 | 9/2002 |
| DE | 121383 | 9/1900 |

(Continued)

OTHER PUBLICATIONS

U.S. Appl. No. 10/857,779, Notice of Allowance dated Jan. 11, 2006, 4 pages.

(Continued)

*Primary Examiner* — Christopher Beccia
(74) *Attorney, Agent, or Firm* — Baker & Hostetler LLP

(57) ABSTRACT

A sternum fixation device for securing parts of a sternum includes first and second removably associated plates. The first plate has an upper surface and a sternum contacting surface, and at least one hole passing through both of these surfaces for receiving a fastener head. The second plate has at least one attachment member for fixation to the sternum. A release member holds the first and second plates together, and is movably associated with at least one of the first and second plates such that it may be moved to allow separation of the two parts of the sternum.

25 Claims, 19 Drawing Sheets

(56) References Cited

U.S. PATENT DOCUMENTS

| | | | |
|---|---|---|---|
| 3,385,299 A | 5/1968 | Le Roy | |
| 3,971,384 A | 7/1976 | Haason | |
| 4,201,215 A * | 5/1980 | Crossett et al. | 606/216 |
| 4,270,248 A | 6/1981 | Akashi | |
| 4,279,248 A | 7/1981 | Gabbay | |
| 4,506,662 A | 3/1985 | Anapliotis | |
| 4,512,346 A | 4/1985 | Lemole | |
| 4,535,772 A | 8/1985 | Sheehan | |
| 4,582,541 A | 4/1986 | Dean et al. | |
| 4,583,541 A | 4/1986 | Barry | |
| 4,593,422 A | 6/1986 | Wolpert, Jr. et al. | |
| 4,653,486 A | 3/1987 | Coker | |
| 4,696,293 A | 9/1987 | Ciullo | |
| 4,730,615 A | 3/1988 | Sutherland et al. | |
| 4,794,675 A | 1/1989 | Bisconti | |
| 4,802,477 A | 2/1989 | Gabbay | |
| 4,813,416 A | 3/1989 | Pollak et al. | |
| 4,852,558 A | 8/1989 | Outerbridge | |
| 4,896,668 A | 1/1990 | Popoff et al. | |
| 4,957,496 A | 9/1990 | Schmidt | |
| 5,006,120 A | 4/1991 | Carter | |
| 5,139,498 A | 8/1992 | Astudillo Ley | |
| 5,167,662 A | 12/1992 | Hayes et al. | |
| 5,263,973 A | 11/1993 | Cook | |
| 5,330,489 A | 7/1994 | Green et al. | |
| 5,339,870 A | 8/1994 | Green et al. | |
| 5,356,412 A | 10/1994 | Golds et al. | |
| 5,356,417 A | 10/1994 | Golds | |
| 5,368,594 A | 11/1994 | Martin et al. | |
| 5,391,168 A | 2/1995 | Sanders et al. | |
| 5,423,821 A | 6/1995 | Pasque | |
| 5,439,463 A * | 8/1995 | Lin | 606/252 |
| 5,454,812 A | 10/1995 | Lin | |
| 5,462,542 A | 10/1995 | Alesi, Jr. | |
| 5,470,333 A | 11/1995 | Ray | |
| 5,527,312 A | 6/1996 | Ray | |
| 5,558,674 A | 9/1996 | Heggeness et al. | |
| 5,611,354 A | 3/1997 | Alleyne | |
| 5,616,142 A | 4/1997 | Yuan et al. | |
| 5,620,444 A | 4/1997 | Assaker | |
| 5,630,815 A | 5/1997 | Pohl et al. | |
| 5,632,724 A | 5/1997 | Lerman et al. | |
| 5,665,089 A | 9/1997 | Dall et al. | |
| 5,667,507 A | 9/1997 | Corin et al. | |
| 5,672,177 A | 9/1997 | Seldin | |
| 5,674,222 A | 10/1997 | Berger et al. | |
| 5,704,936 A | 1/1998 | Mazel | |
| 5,707,372 A | 1/1998 | Errico et al. | |
| 5,749,873 A | 5/1998 | Fairley | |
| 5,766,218 A | 6/1998 | Arnott | |
| 5,800,433 A | 9/1998 | Benzel et al. | |
| 5,810,822 A | 9/1998 | Mortier | |
| 5,827,286 A | 10/1998 | Incavo et al. | |
| 5,849,012 A | 12/1998 | Abboudi | |
| 5,891,144 A | 4/1999 | Mata et al. | |
| 5,902,304 A | 5/1999 | Walker et al. | |
| 5,928,231 A | 7/1999 | Klein et al. | |
| 5,941,881 A | 8/1999 | Barnes | |
| 5,964,762 A | 10/1999 | Biedermann et al. | |
| 5,964,763 A | 10/1999 | Incavo et al. | |
| 5,993,452 A | 11/1999 | Vandewalle | |
| 6,007,536 A | 12/1999 | Yue | |
| 6,007,538 A * | 12/1999 | Levin | 606/71 |
| 6,024,759 A | 2/2000 | Nuss et al. | |
| 6,045,572 A | 4/2000 | Johnson et al. | |
| 6,051,007 A * | 4/2000 | Hogendijk et al. | 606/151 |
| 6,053,915 A | 4/2000 | Bruchmann | |
| 6,066,141 A | 5/2000 | Dall et al. | |
| 6,066,142 A | 5/2000 | Serbousek et al. | |
| 6,117,135 A | 9/2000 | Schläpfer | |
| 6,129,728 A | 10/2000 | Schumacher et al. | |
| 6,139,316 A | 10/2000 | Sachdeva et al. | |
| 6,139,548 A | 10/2000 | Errico | |
| 6,139,550 A | 10/2000 | Michelson | |
| 6,187,004 B1 | 2/2001 | Fearon | |
| 6,200,318 B1 | 3/2001 | Har-Shai et al. | |
| 6,206,828 B1 | 3/2001 | Wright | |
| 6,217,580 B1 | 4/2001 | Levin | |
| 6,238,396 B1 | 5/2001 | Lombardo | |
| 6,306,136 B1 * | 10/2001 | Baccelli | 606/279 |
| 6,355,036 B1 | 3/2002 | Nakajima | |
| 6,432,108 B1 | 8/2002 | Burgess et al. | |
| 6,540,769 B1 | 4/2003 | Miller, III | |
| 6,623,486 B1 | 9/2003 | Weaver et al. | |
| 6,656,179 B1 | 12/2003 | Schaefer et al. | |
| 6,666,867 B2 | 12/2003 | Ralph et al. | |
| 6,689,134 B2 | 2/2004 | Ralph et al. | |
| 6,712,821 B2 | 3/2004 | Gabbay | |
| 6,786,910 B2 | 9/2004 | Cohen et al. | |
| 6,872,210 B2 | 3/2005 | Hearn | |
| 7,033,377 B2 | 4/2006 | Miller, III | |
| 7,331,781 B1 | 2/2008 | Bandeen | |
| 7,399,301 B2 | 7/2008 | Michelson | |
| 8,221,421 B2 | 7/2012 | Hearn | |
| 2003/0083694 A1 | 5/2003 | Miller, III | |

FOREIGN PATENT DOCUMENTS

| | | |
|---|---|---|
| DE | 9321544 | 9/1999 |
| EP | 0354599 A1 | 2/1990 |
| EP | 0583520 A1 | 2/1994 |
| EP | 0958786 A2 | 11/1999 |
| EP | 1365639 | 11/2003 |
| FR | 2704420 A1 | 11/1994 |
| FR | 2720623 A1 | 12/1995 |
| JP | 64043249 | 3/1989 |
| JP | 05220174 A | 8/1993 |
| JP | 09206310 A | 8/1997 |
| JP | 11070125 A | 3/1999 |
| JP | 11290338 A | 10/1999 |
| JP | 11299804 A | 11/1999 |
| JP | 2001-037767 | 2/2001 |
| WO | WO 92/01428 A1 | 2/1992 |
| WO | WO 96/00529 A1 | 1/1996 |
| WO | WO 96/32072 A1 | 10/1996 |
| WO | WO 96/36391 A2 | 11/1996 |
| WO | WO 98/44850 A1 | 10/1998 |

OTHER PUBLICATIONS

English Abstract of FR 2704420 A1 of Innovations Technologiques Ste dated Nov. 4, 1994.
English Abstract of FR 2720623 A1 of Implants Orthopediques Toutes dated Dec. 8, 1995.
English Abstract of JP 05220174 A of Shima Yumiko dated Aug. 31, 1993.
English Abstract of JP 09206310 A of NGK Spark Plug Co. dated Aug. 12, 1997.
English Abstract of JP 11070125 A of United States Surgical Corp. dated Mar. 16, 1999.
English Abstract of JP 11290338 A of Medical U & A KK dated Oct. 26, 1999.
English Abstract of JP 11299804 A of Homuzu Giken KK dated Nov. 2, 1999.

* cited by examiner

STERNUM FIXATION DEVICE

CROSS-REFERENCE TO RELATED APPLICATIONS

This application is a continuation of, and claims priority to, U.S. patent application Ser. No. 11/030,507, filed Jan. 5, 2005, which issued as U.S. Pat. No. 8,221,421. U.S. patent application Ser. No. 11/030,507 is division of, and claims priority to, U.S. patent application Ser. No. 10/073,133, filed Feb. 13, 2002, which issued as U.S. Pat. No. 6,872,210. U.S. patent application Ser. No. 10/073,133 claims priority to U.S. provisional patent application No. 60/270,620, filed Feb. 23, 2001. U.S. patent application Ser. No. 11/030,507, U.S. patent application Ser. No. 10/073,133, and U.S. provisional patent application No. 60/270,620 are incorporated herein by reference in their respective entireties.

FIELD OF THE INVENTION

The present invention relates generally to surgical devices, and more particularly, to devices for reapproximating two or more parts of a patient's sternum.

BACKGROUND

Many surgical procedures require two or more parts of a sternum to be reapproximated, or fixed together, such as sternal reconstruction and repair of sternal trauma. In addition, various types of surgical procedures are currently performed to investigate, diagnose, and treat diseases involving tissues or organs located in a patient's thoracic cavity, such as the heart and lungs. These procedures typically require a partial or median sternotomy to gain access to the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs, vessels, or tissues. Following the surgical procedure within the thoracic cavity, the two severed sternal halves must be reapproximated.

Sternum fixation has traditionally been performed using stainless steel wires that are wrapped around or through the sternal halves and then twisted together, so as to compress the two halves together. Other methods of sternum fixation include the use of band or strap assemblies. Such assemblies typically include a locking mechanism, which secures a strap in a closed looped configuration around the sternum halves. While utilization of steel wires and strap assemblies have been widely accepted for sternum fixation, these devices present a number of disadvantages. For example, steel wires are susceptible to breakage, are difficult to maneuver and place around the sternum, and often have sharp ends that can pierce through the surgeon's gloves or fingers. Steel wire and band assemblies also provide insufficient or non-uniform clamping force on the sternal halves, thus resulting in sternal nonunion. The steel wire and band assemblies also provide insufficient clamping forces in all three planar directions, thus leading to healing problems caused by unwanted bone movements leading to raking and rubbing of the surrounding tissue or bone.

Several other techniques of sternal fixation have been developed for reapproximating the sternal halves. One technique uses plates that are located on both sternal halves across the sternotomy and are fixed thereto by means of screws through the bone on either side of the sternotomy. This technique, however, is not optimal because it requires direct fixation of the plates to the bone with screws, making reentry into the thoracic cavity through the sternotomy extremely difficult in case of a medical emergency.

Another technique uses a sternal clamp having a pair of opposed generally J-shaped clamp members which are laterally adjustable relative to one another but can be rigidly joined with a set of machine screws. Similar to the use of plates, discussed above, this technique does not provide quick access to the organs and/or tissues within the patient's thoracic cavity.

Yet another fixation device comprises a pair of hook-shaped clamps that slide together and lock in position with respect to one another using a ratchet assembly. The ratchet assembly provides quickened accesses to the thoracic cavity, but is cumbersome to use and is limited to the hook-shaped clamp members disclosed.

Therefore, it is desirable to provide a sternum fixation device that stabilizes the sternum in all three planar directions, has a fast and easy to use quick-release feature, and works in several different configurations.

SUMMARY

The present invention is directed to a sternum fixation device for securing parts of a sternum. The sternum fixation device includes a first plate and a second plate. The first plate has an upper surface and a sternum-contacting surface, at least one hole passing through the upper and sternum-contacting surfaces for receiving a fastener head of a bone fastener, and a first longitudinal bore defining an axis oriented substantially transversely to the at least one hole. The at least one hole may be threaded to receive a threaded fastener head. The second plate has an upper surface and a sternum-contacting surface, an attachment member for fixation to the sternum, and a second longitudinal bore. The first and second plates are dimensioned to mate with one another such that the first and second longitudinal bores are aligned to receive the release member, and removal of the release member from the first and second longitudinal bores allows separation of the two parts of the sternum. The first and second plates mate with one another such that they cannot rotate with respect to one another about the release member.

According to one aspect of the present invention, the release member is a pin, which may be a single pronged pin. The pin may have a splayed apart tip portion. Alternatively, the release member is a two pronged pin, which may be angled with respect to a mating line between the first and second plates. The release member may also be a cam or quarter-turn fastener, and the first and second plates may be provided with matching sets of ratchet teeth that cooperate with the release member to allow the distance between the first and second plates to be varied.

The attachment member may be a threaded through hole that passes through the second plate upper and sternum-contacting surfaces for receiving a threaded fastener head. To increase pull-out resistance of the fastener, the at least one threaded hole may be angled away from the second plate.

According to another embodiment of the present invention, the attachment member is a hook member for engaging an intercostal space portion of the sternum. Preferably, the attachment member comprises at least two hook members that are spaced apart by an adjustable lateral distance. Alternate embodiments include multiple combinations of fastener and hook-shaped attachment members.

DETAILED DESCRIPTION

Figure 1:
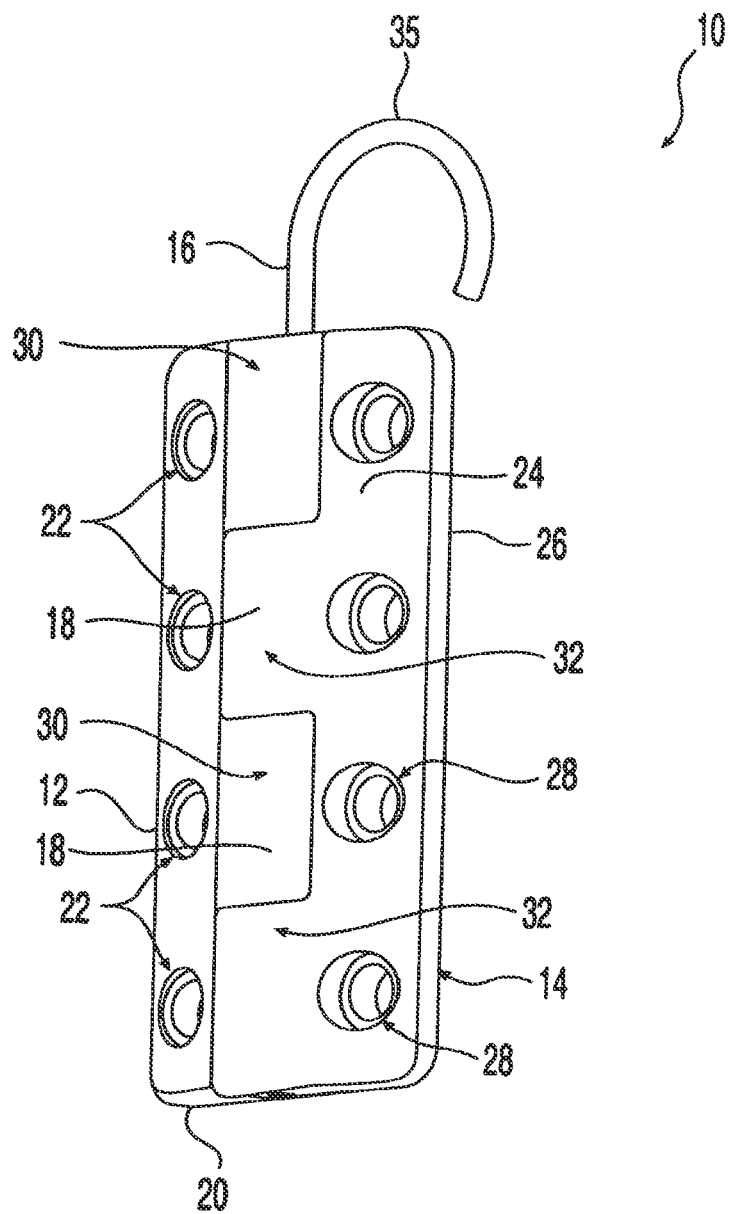
FIG. 1 is a perspective view of a first embodiment of a sternum fixation device according to the present invention.
Figure 2:
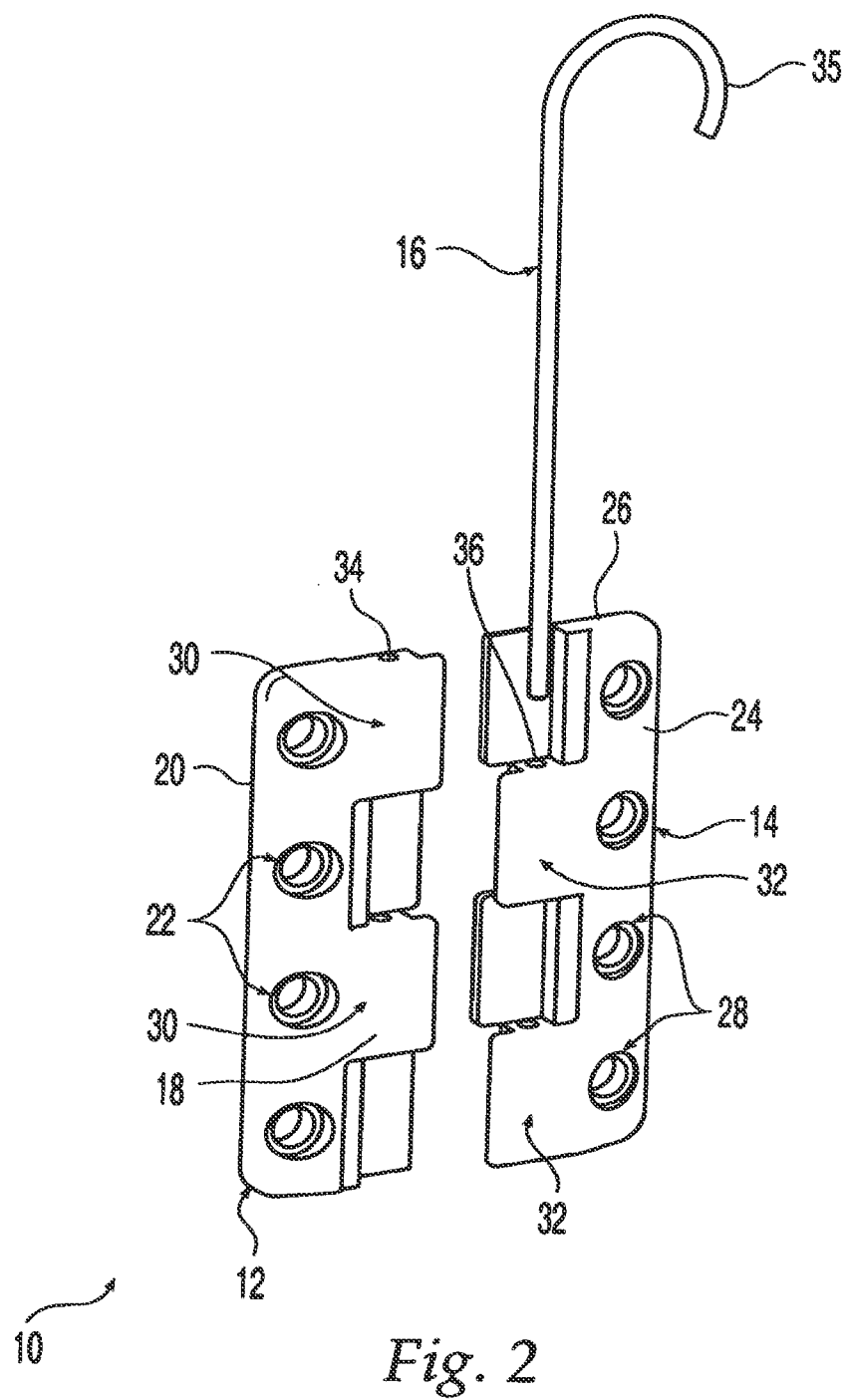
FIG. 2 is an exploded perspective view of the sternum fixation device of FIG. 1.
Figure 19:
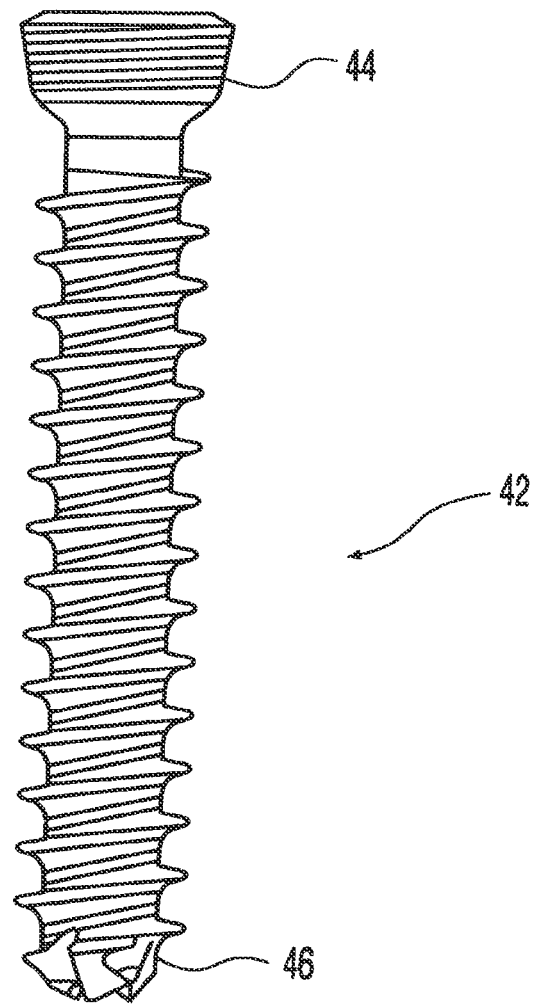
FIG. 19 is an elevation view of a bone fastener having a threaded head portion for use with one embodiment of the first and second attachment members according to the present invention.

FIGS. 1 and 2 show a first illustrative embodiment of a sternum fixation device according to the present invention, shown as sternum fixation device 10. Sternum fixation device 10 includes first and second mating plates 12, 14 attached to one another by a release member 16. First plate 12 and second plate 14 may be used to reapproximate, or secure together, two or more parts of a sternum by attaching each plate to a part of the sternum. Sternum fixation device 10 may be constructed from any suitable bio-compatible material including, but not limited to, bioresorbable materials, radio-translucent materials, allograft materials, stainless steel and titanium First plate 12 includes an upper surface 18 and a sternum-contacting surface 20, and a first attachment member 22 for attachment to the sternum. First attachment member 22 is shown as a plurality of threaded holes that are configured to receive a threaded head portion 44 of a fastener, such as a bone screw 42, shown in FIG. 19. The fastener may alternatively have an elongated shaft with barbs formed thereon that anchor the fastener in the bone. Second plate 14 includes an upper surface 24 and a sternum-contacting surface 26, and a second attachment member 28, also shown as a plurality of threaded holes for receiving a threaded head portion of a bone screw 42. Alternatively, the holes of the first and second attachment members 22, 28 may not have threads and receive a non-threaded head portion of a fastener. Sternum-contacting surfaces 20, 26 may be scalloped, or provided with various other surface treatments that are known by one of ordinary skill in the bone plating art to minimize the contact area between the first and second plates 12, 14 and the respective parts of the sternum.

First plate 12 further includes a series of first joining portions 30 that interdigitate with corresponding second joining portions 32 on second plate 14. A first longitudinal bore 34 extends through the first joining portions 30 and a second longitudinal bore 36 extends through the second joining portions 32 such that when first plate 12 and second plate 14 are positioned adjacent one another with the first and second joining portions 30, 32 interdigitated, the first and second longitudinal bores 34, 36 are substantially aligned and may receive release member 16. Alternatively, the first and second joining portions 30, 32 could be provided with multiple sets of aligned longitudinal bores to allow the distance between the first and second attachment members 22, 28 to be varied to accommodate a range of sternum sizes.

As shown in FIGS. 1 and 2, release member 16 is shown as an elongated pin having a curved grip portion 35. Release member 16 could alternatively have a T-shaped grip portion. When inserted into aligned first and second longitudinal bores 34, 36, release member 16 secures the first and second plates 12, 14 together. As shown in FIG. 2, when the release member 16 is removed from the first and second longitudinal bores 34, 36, the first and second plates 12, 14 are allowed to separate. Thus, release member 16 can be removed from the first and second longitudinal bores 34, 36 to quickly and conveniently gain access to the thoracic cavity. This quick release mechanism can be useful, for example, in the case of a medical emergency.

According to one aspect of the present invention, first and second joining portions 30, 32 may be configured such that the first and second plates 12, 14 cannot rotate with respect to one another about the release member 16, thus providing increased stabilization of the two parts of the sternum. As shown in FIG. 2, the first and second joining portions 30, 32 overlap as well as interdigitate, thus fixing the plates together such that they do not rotate with respect to one another. As an alternative to overlapping the joining portions, release member 16 may be configured to prevent relative rotation between the first and second plates 12, 14. For example, release member 16 and the first and second longitudinal bores 34, 36 may have matching polygonal cross-sections, such as rectangular, square, or triangular, which prevent rotation of either of the plates 12, 14 relative to the release member 16 and consequently, relative to one another. The matching cross-sections may also be ovular. Alternatively, release member 16 may be a multi-pronged pin and the first and second joining portions 30, 32 may be provided with multiple sets of aligned longitudinal bores. One of ordinary skill in the bone plating art, however, will know and appreciate than any number of configurations may be used to prevent rotation between the first and second plates 12, 14.

Figure 3:
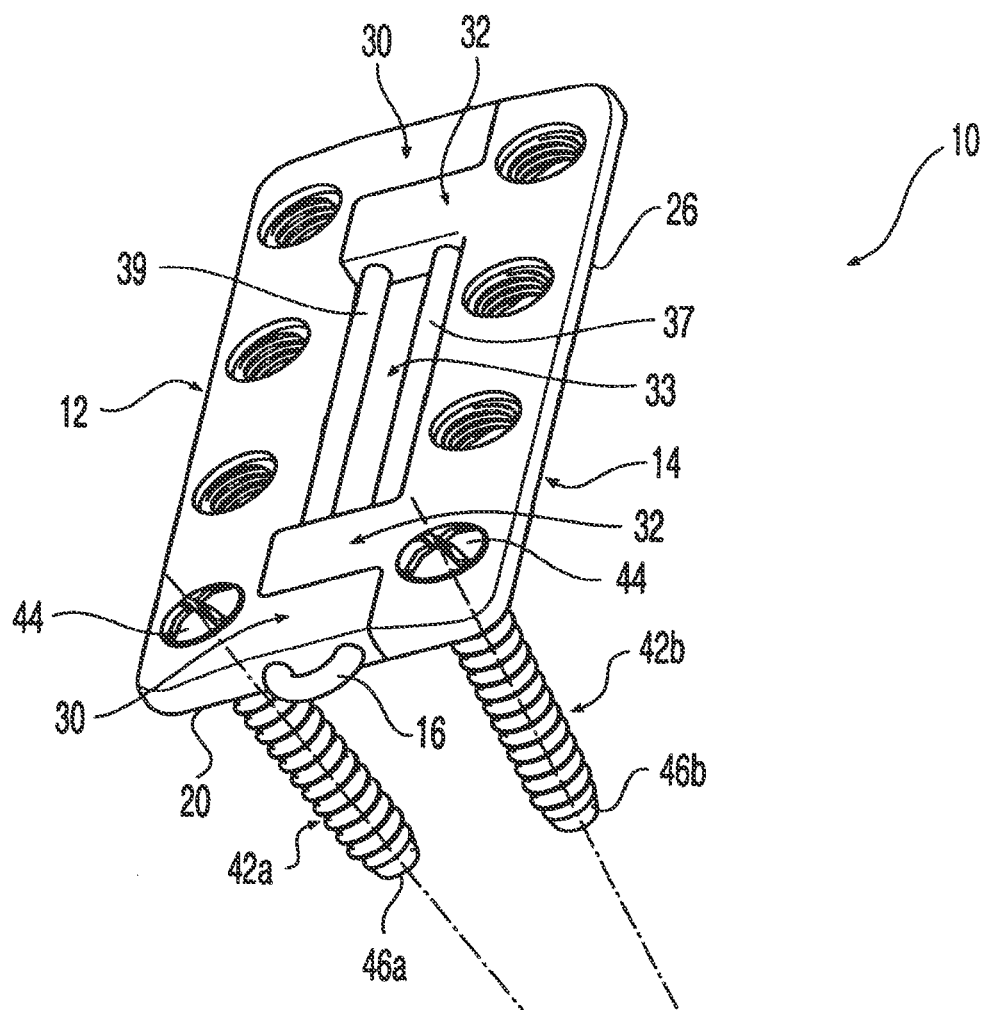
FIG. 3 is a perspective view of the sternum fixation device of FIG. 1, having a U-shaped release member.
Figure 4:
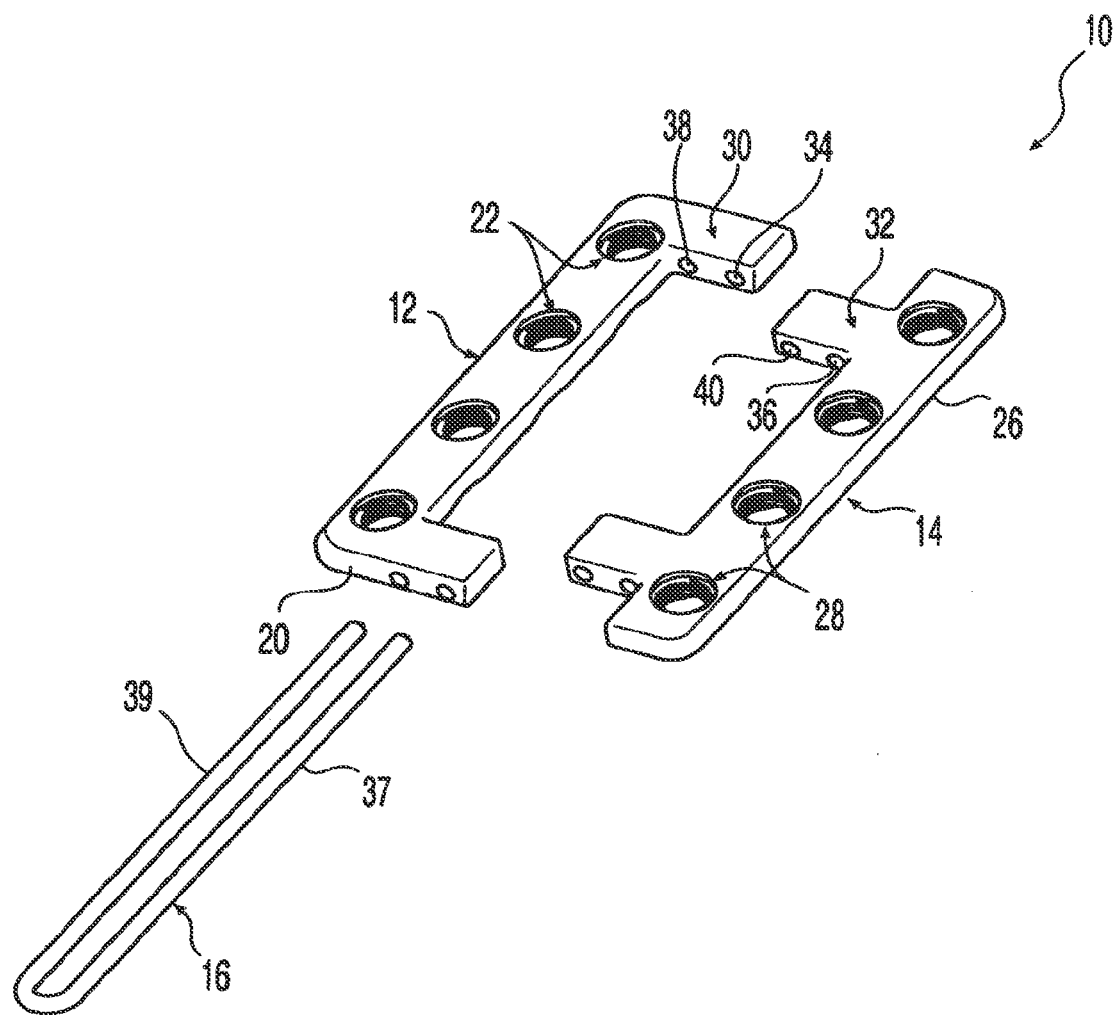
FIG. 4 is an exploded perspective view of the sternum fixation device of FIG. 3.

Referring to FIGS. 3 and 4, a variation of sternum fixation device 10 is shown with release member 16 in the form of a U-shaped pin having spaced apart leg portions 37, 39. The first and second plates 12, 14 have first and second joining portions 30, 32 that are spaced apart such that a central opening 33 is defined between the first and second plates 12, 14. Central opening 33 serves to minimize the amount of implanted material that contacts the sternum. A third longitudinal bore 38 extends through the first mating portion 30 and a fourth longitudinal bore 40 extends through the second mating portion 32. The third and fourth longitudinal bores 38, 40 are located such that when the first plate 12 and second plate 14 are positioned adjacent one another with the first and second joining portions 30, 32 interdigitated, the first and second longitudinal bores 34, 36 are substantially aligned, as are the third and fourth longitudinal bores 38, 40. Thus, each of the release member leg portions 37, 39 may be received in one of the aligned pairs of bores to secure the first and second plates 12, 14 together. The spaced apart relationship of leg portions 37, 39 and the respective sets of aligned longitudinal bores prevents the first and second plates 12, 14 from rotating with respect to one another about the release member 16, thus stabilizing the sternum fixation device 10.

Still referring to FIGS. 3 and 4, the first and second attachment members 22, 28 are in the form of a plurality of threaded holes configured to receive a threaded head 44 of a bone screw 42. To reduce the tendency of the bone screws 42 to pull out of the sternum, the threaded holes of the first attachment member 22 and the second attachment member 28 may be angled such that the threaded tip portions 46 of opposing bone screws, for example, bone screws 42a and 42b, are angled towards one another.

Figure 5:
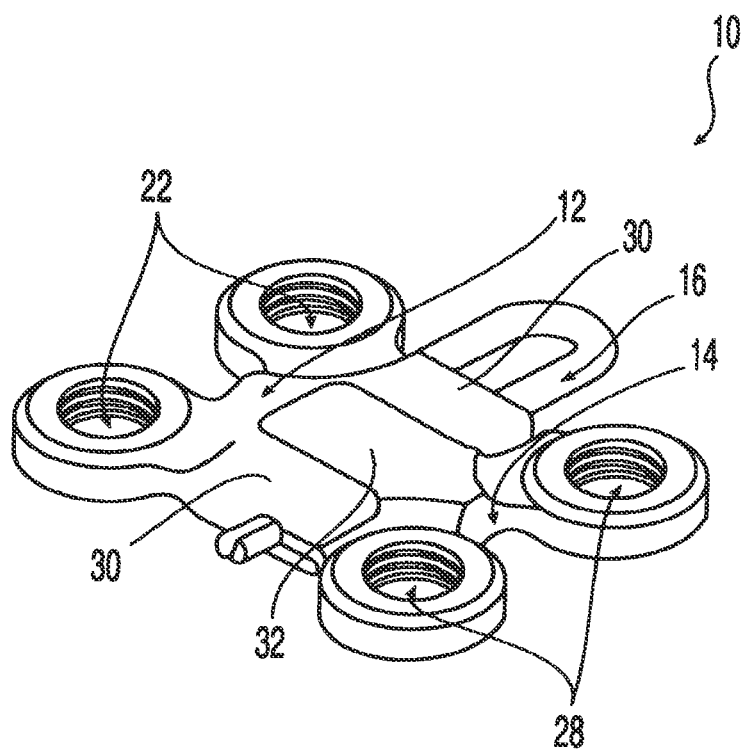
FIG. 5 is a perspective view of the sternum fixation device of FIG. 1, having differently shaped first and second mating portions.
Figure 6:
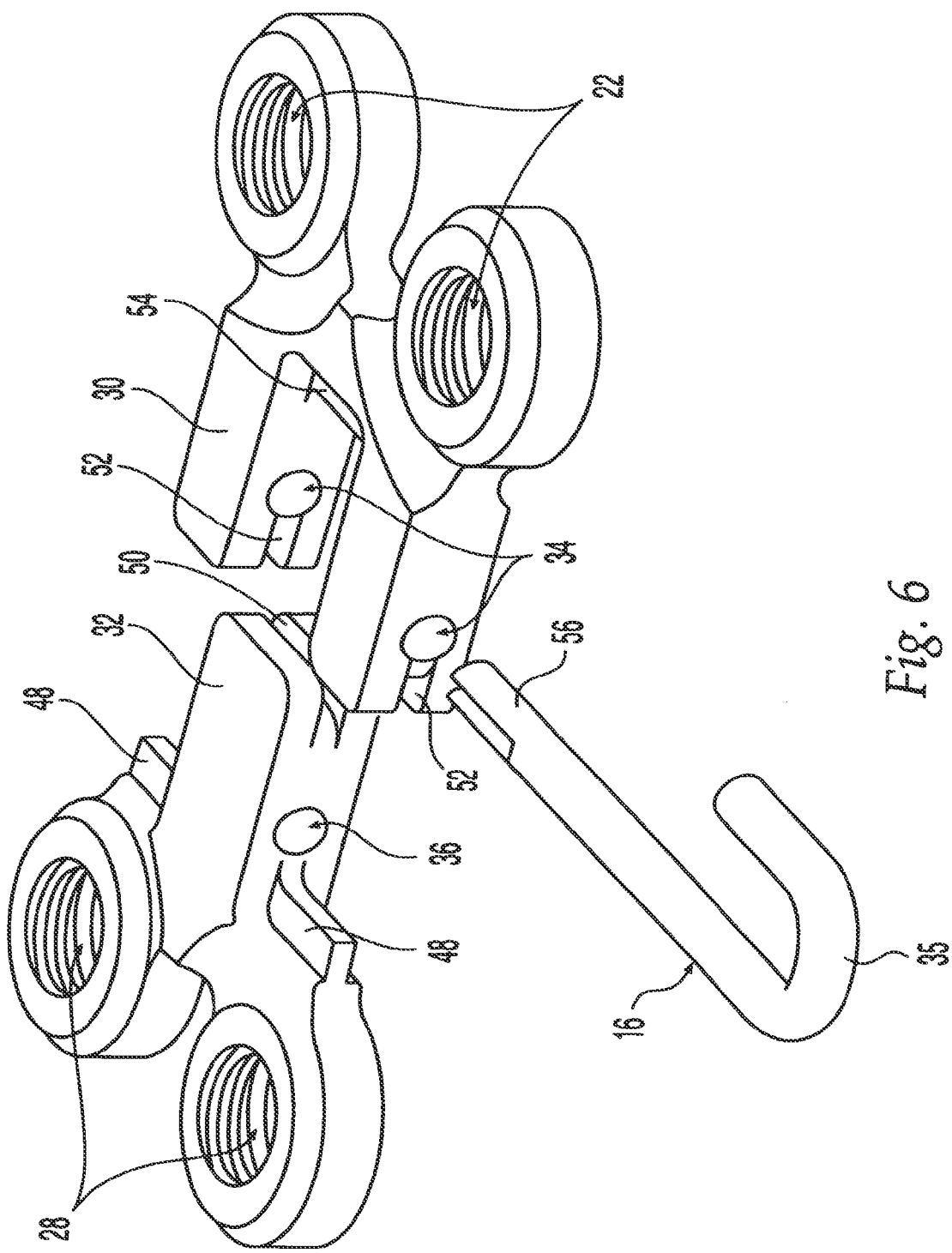
FIG. 6-7 are exploded perspective views of the sternum fixation device of FIG. 5, showing variations of the first and second mating portions and release member.
Figure 7:
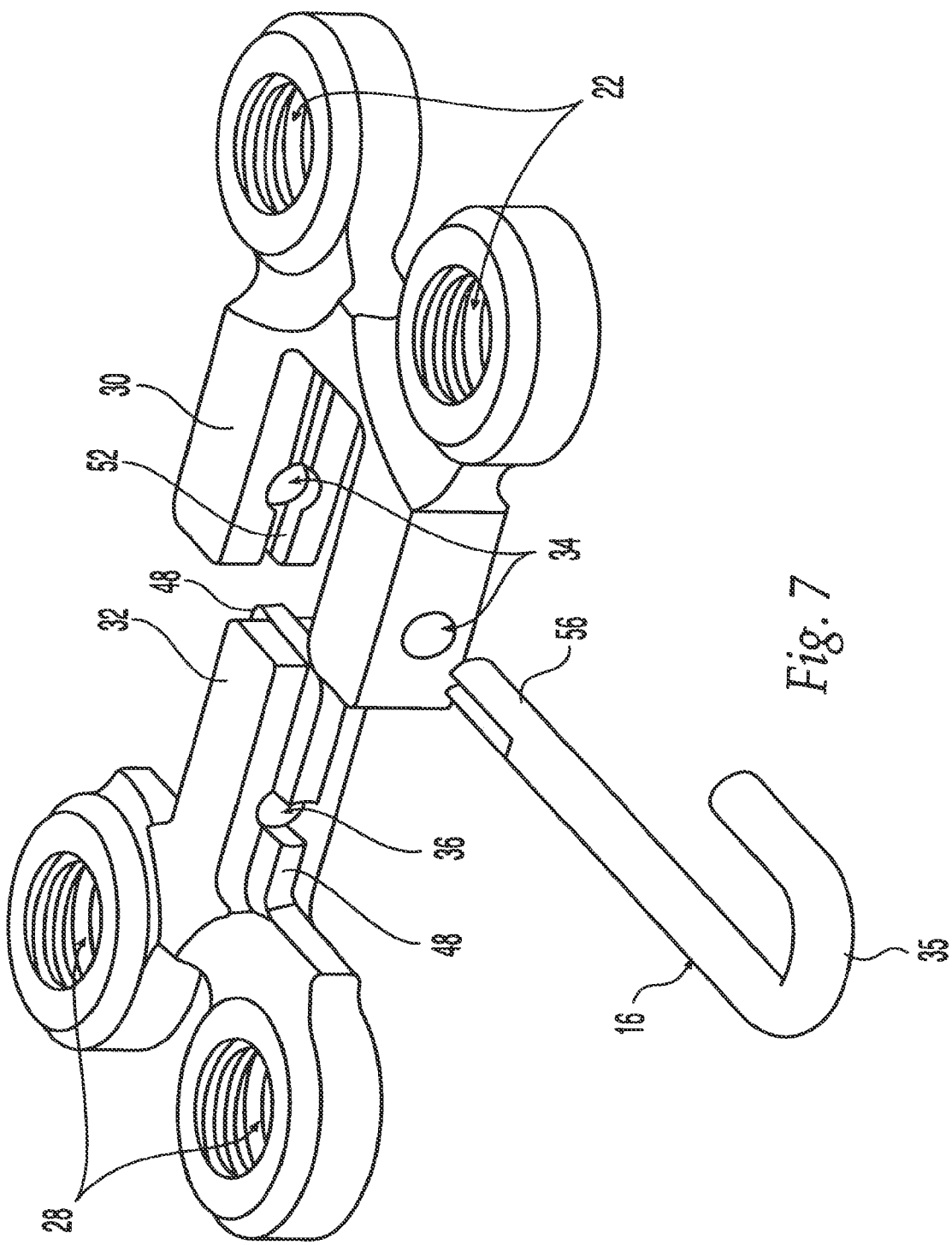

FIGS. 5-12 show several additional variations of sternum fixation device 10. In each of the variations shown, first and second plates 12, 14 are reduced in size so that they outline the first and second attachment members 22, 28, thereby reducing the amount of material that contacts the sternum. Referring to FIGS. 5, 6 and 7, the first and second joining portions 30, 32 may each have protrusions and/or indentations formed thereon to prevent them from rotating with respect to one another. As shown in FIG. 6, second joining portion 32 includes transverse tabs 48 and groove 50, and first joining portion 30 has mating grooves 52 and tab 54 formed thereon, which cooperate to prevent rotation between the first and second plates 12, 14. Release member 16 has a resiliently expanded, or splayed, tip portion 56 that provides resistance against the release member 16 coming out of first and second longitudinal bores 34, 36. Release member 16 may alternatively be a taper pin. As shown in FIG. 7, tabs 48 and grooves 52 may be oriented parallel to the joining portions, however, one of ordinary skill in the bone plating art will know and appreciate that any number of configurations of mating protrusions and/or indentations may be formed on the first and second mating portions 30, 32 to prevent rotation between them.

Figure 8:
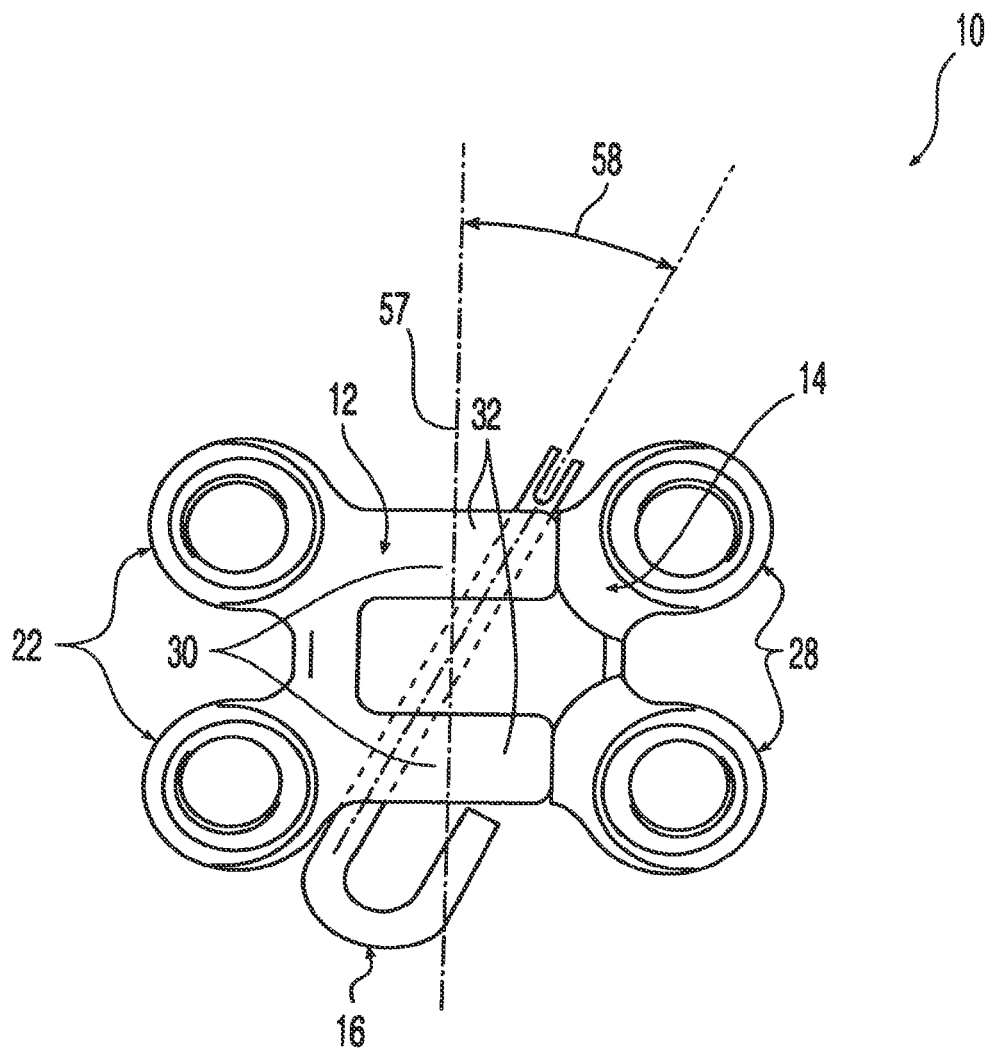
FIG. 8 is an elevation view of the sternum fixation device of FIG. 5, wherein the release member is angled with respect to a mating line between the first and second plates.
Figure 9:
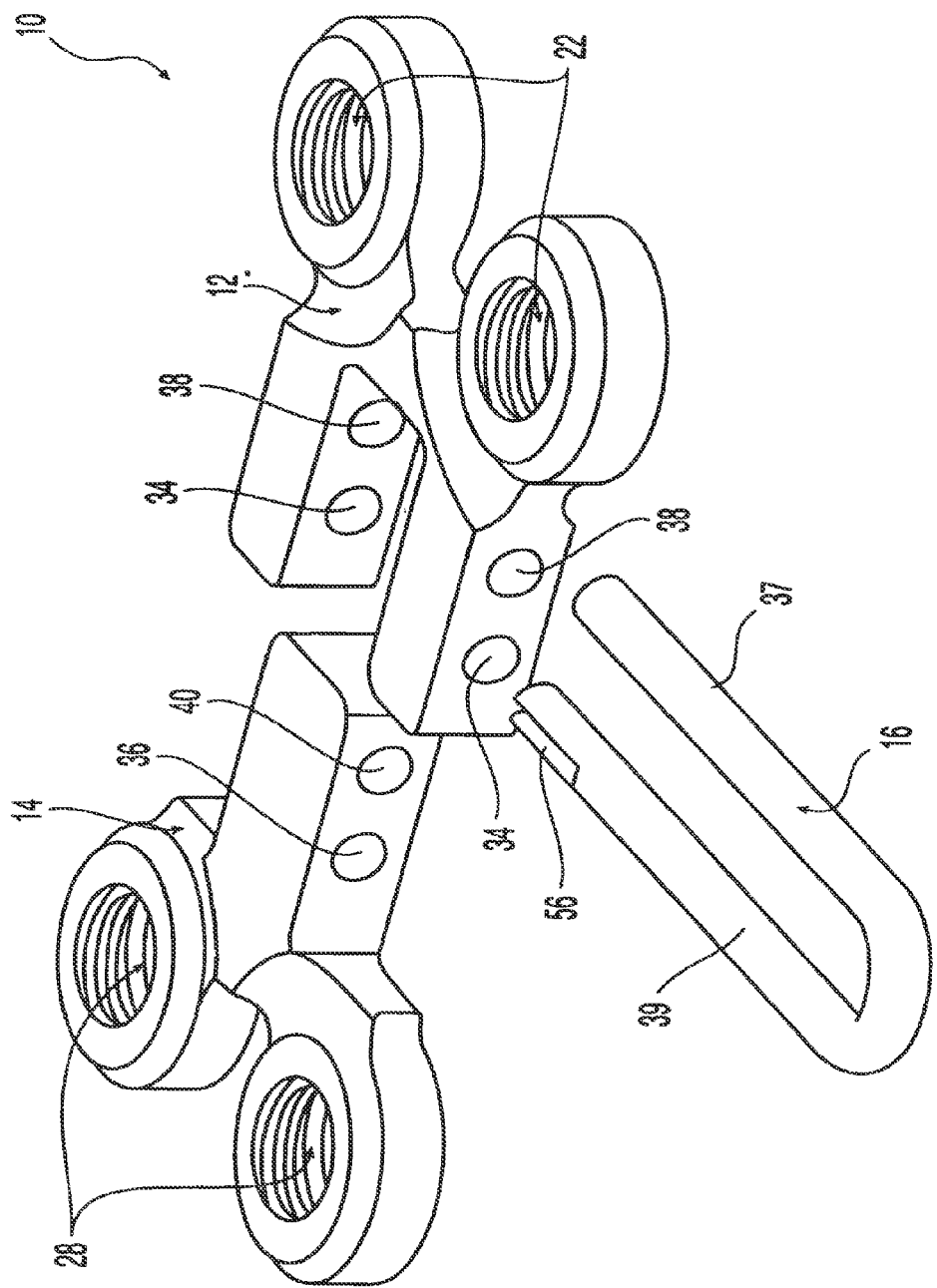
FIG. 9 is a perspective view of the sternum fixation device of FIG. 1, having differently shaped first and second mating portions.
Figure 10:
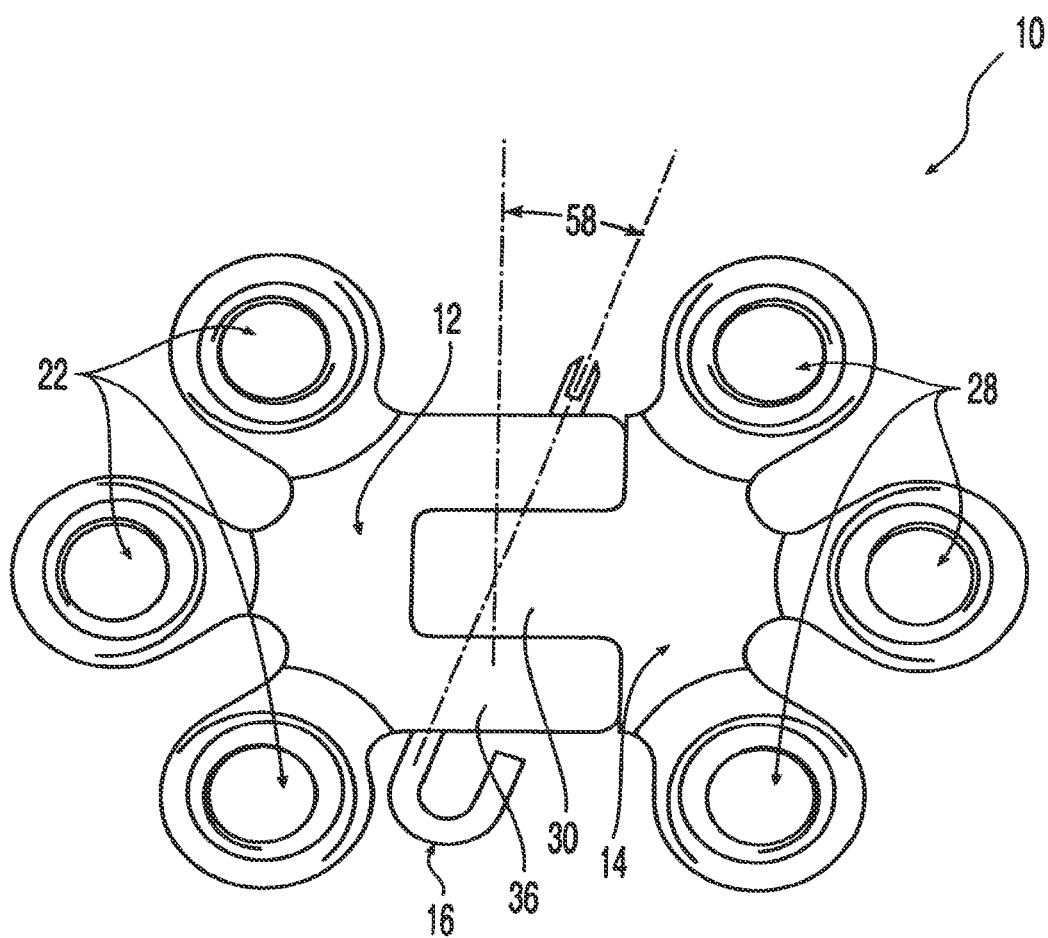
FIG. 10-12 are elevation views of the sternum fixation device of FIG. 5, having additional first and second attachment members.
Figure 11:
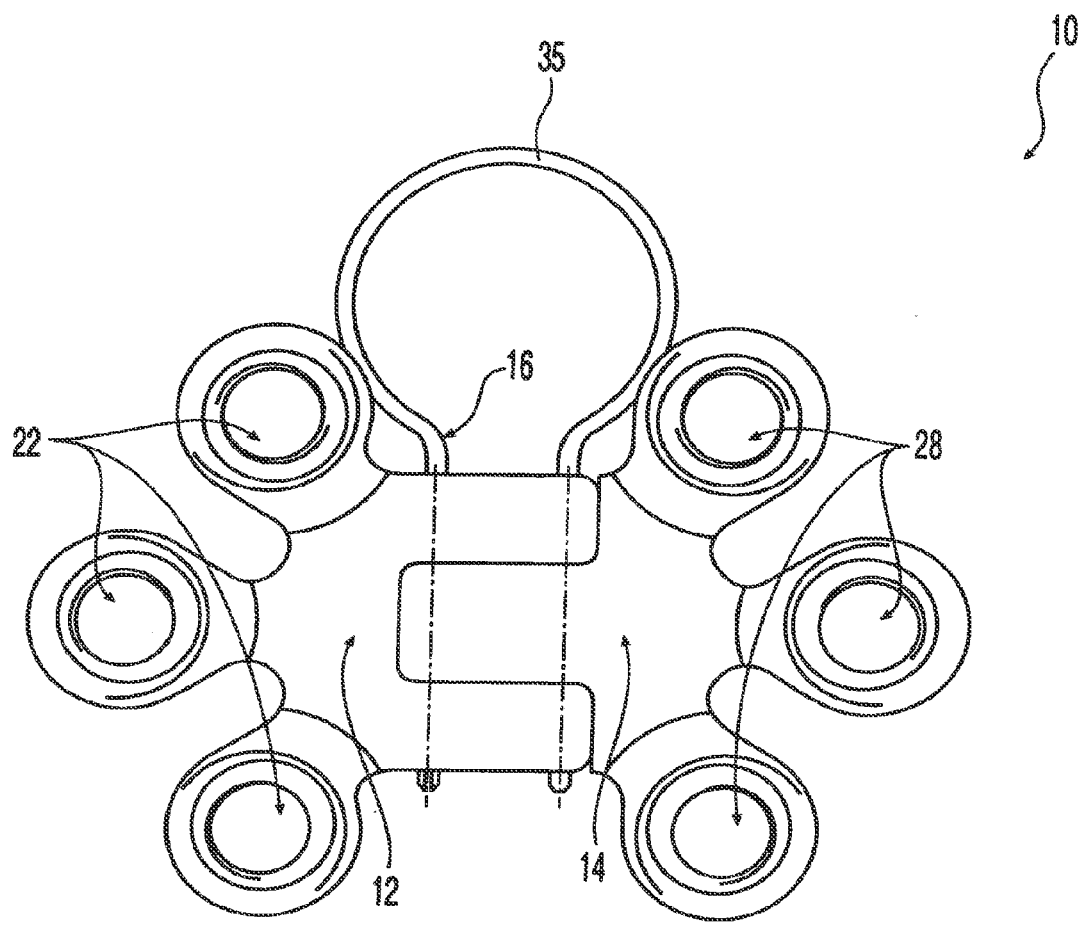
Figure 12:
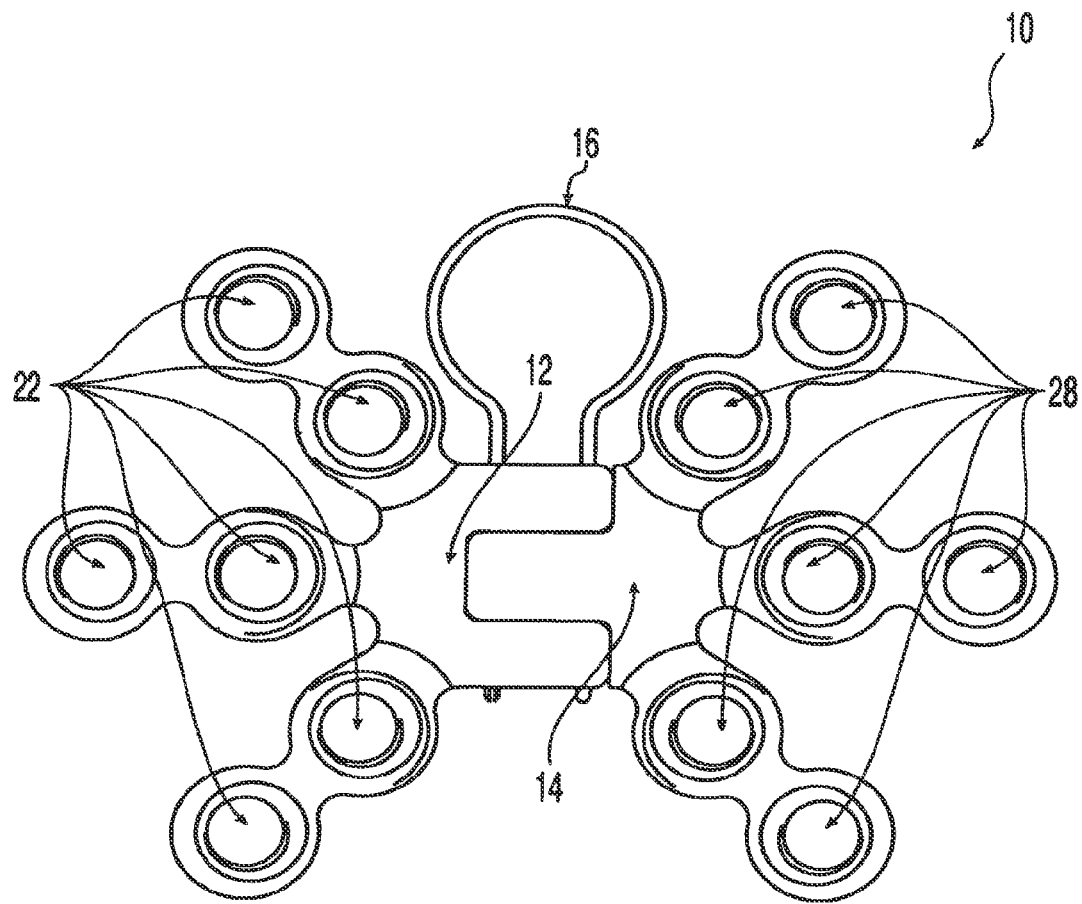
Figure 13:
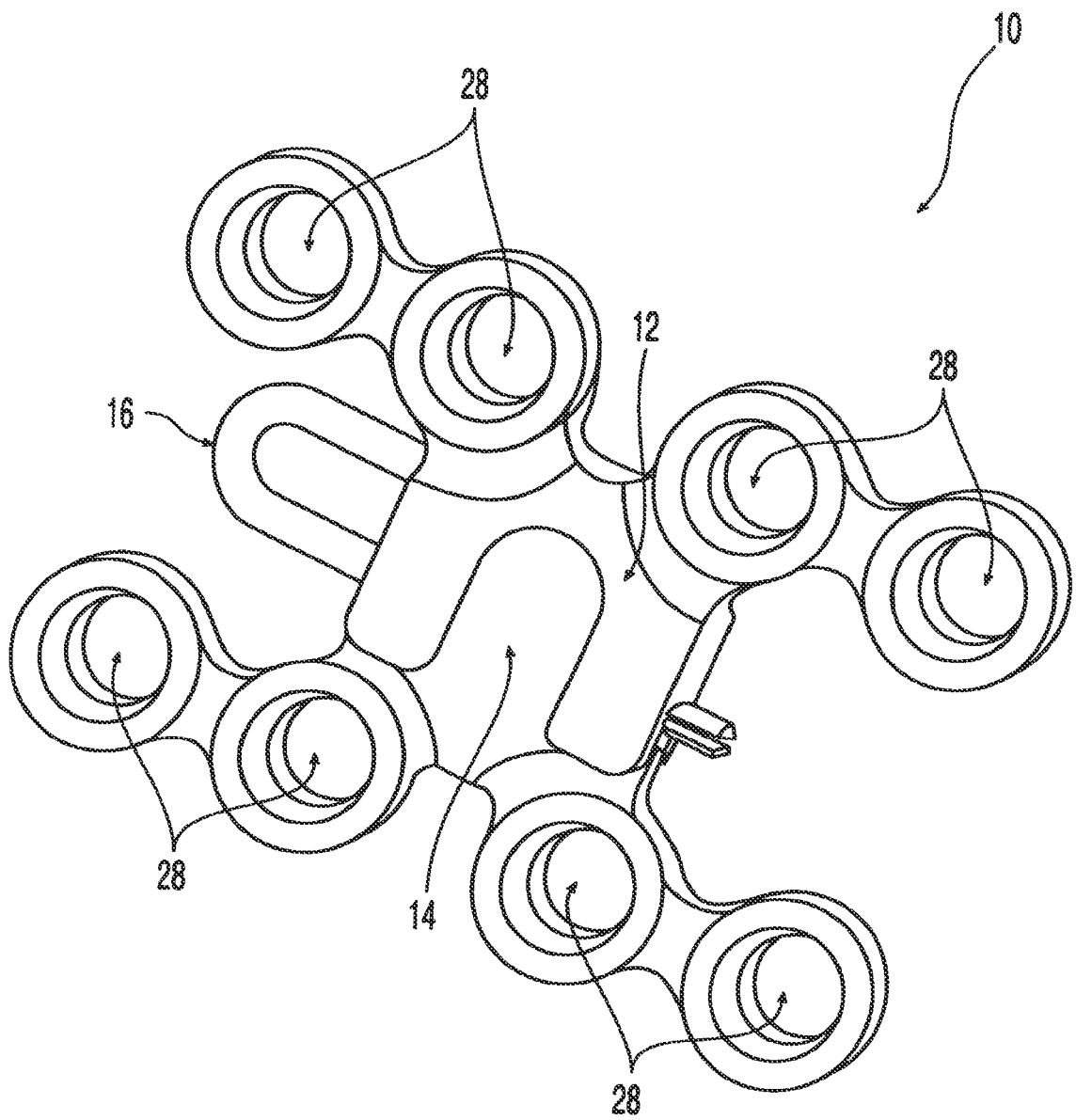
FIG. 13 is a perspective view of the sternum fixation device of FIG. 5, having additional first and second attachment members.

FIG. 8 shows a variation of sternum fixation device 10 wherein the first and second longitudinal bores 34, 36 are oriented at an angle 58 to the intersection 57 of first and second plates 12, 14. When release member 16 is received in aligned first and second longitudinal bores 34, 36 (hidden in FIG. 8), the skewed orientation of release member 16 with respect to intersection 57 prevents rotation between the first and second plates 12, 14. FIG. 9 shows another variation of sternum fixation device 10 having a release member 16 in the form of a U-shaped pin, as discussed above with respect to FIGS. 3 and 4. Release member 16 could alternatively be a V-shaped pin, a T-shaped pin, or any other shape known to one of ordinary skill in the art. FIG. 10 shows a variation of sternum fixation device 10 having first and second attachment members 22, 28 comprising three threaded fastener or screw holes each, and a skewed release member 16. FIG. 11 shows another variation having a U-shaped release member 16 with an enlarged ring-shaped grip portion 35. FIG. 12 shows yet another variation where first attachment member 22 and second attachment member 28 each comprise six threaded fastener or screw holes for receiving a threaded head 44 of a bone fastener or bone screw 42. FIG. 13 shows a variation where the first attachment member 22 and the second attachment member 28 are arranged in an H-shaped pattern. One of ordinary skill in the bone plating art will know and appreciate that any of the features and variations described above may be combined to produce a sternum fixation device according to the present invention.

Figure 14:
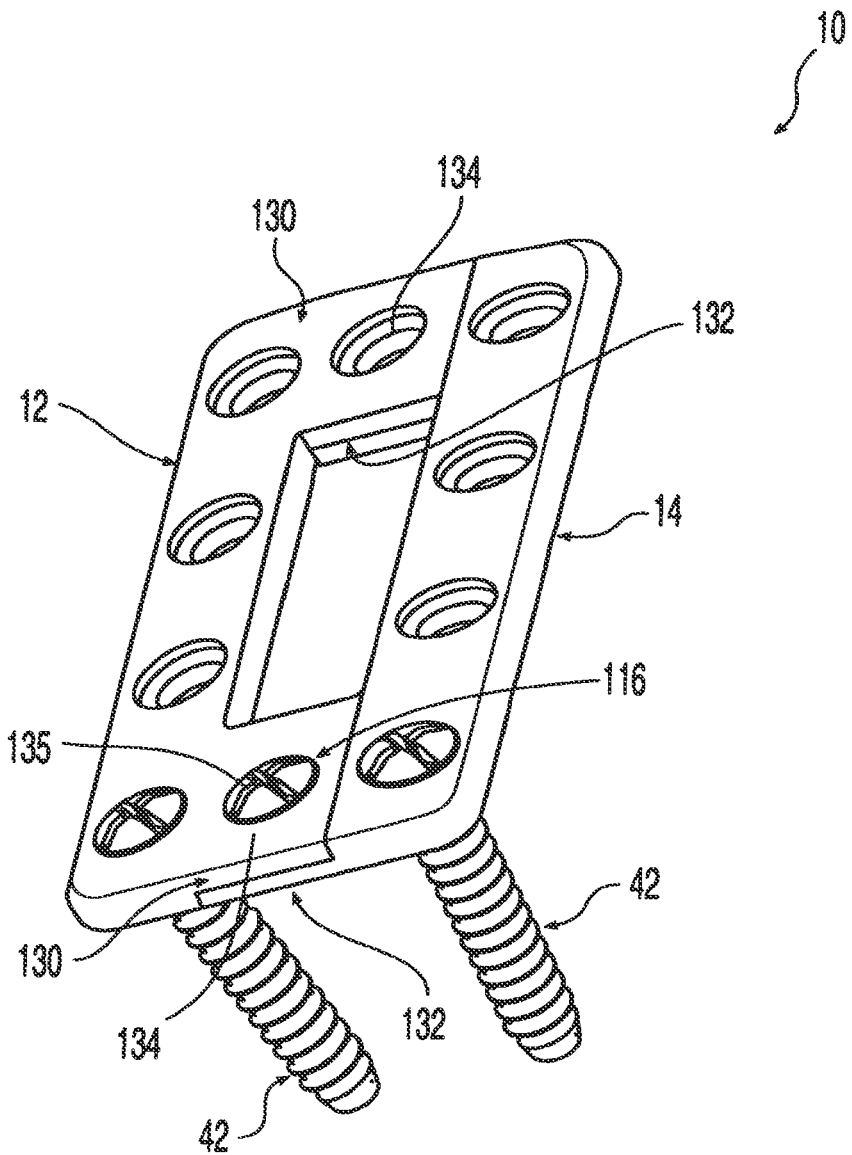
FIG. 14 is a perspective view of a sternum fixation device of FIG. 1, having an alternate embodiment of the release member of FIG. 1.

FIG. 14, shows an alternate embodiment of a release member 116 according to the present invention, which comprises a pair of quarter-turn fasteners or screws, or other cam-type screws known by one of ordinary skill in the art. The first joining portions 130 each have a countersunk bore 134 for receiving a head 135 of the release member 116, and the second joining portions 132 each have a threaded bore, or cam surface 136 (hidden in FIG. 14), for receiving a threaded or cam portion 137 (hidden in FIG. 14) of the release member 116, or vice versa. The first joining portions 130 overlap the second joining portions 132, or vice versa, such that the release member 116 can be inserted through the countersunk bore 134 and be received by cam surface 136 to secure the first and second plates 12, 14 together. To separate the first and second plates 12, 14 the release member 116 is rotated through a predetermined angle preferably of less than 360 degrees, such as, for example ninety degrees, to release the cam portion 137 of the release member 116 from the cam surface 136 and allow the first and second plates 12, 14 to come apart.

Figure 15:
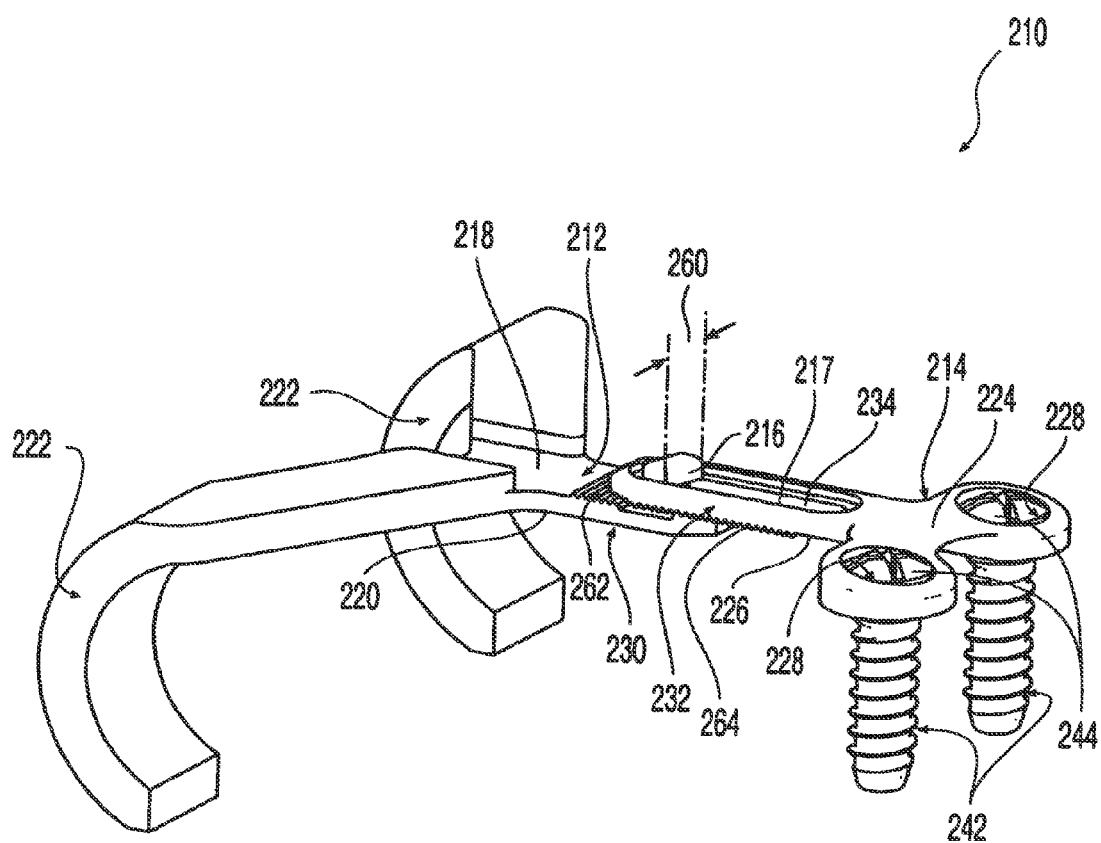
FIG. 15 is a perspective view of a second embodiment of a sternum fixation device according to the present invention, having hook-shaped attachment members.
Figure 16:
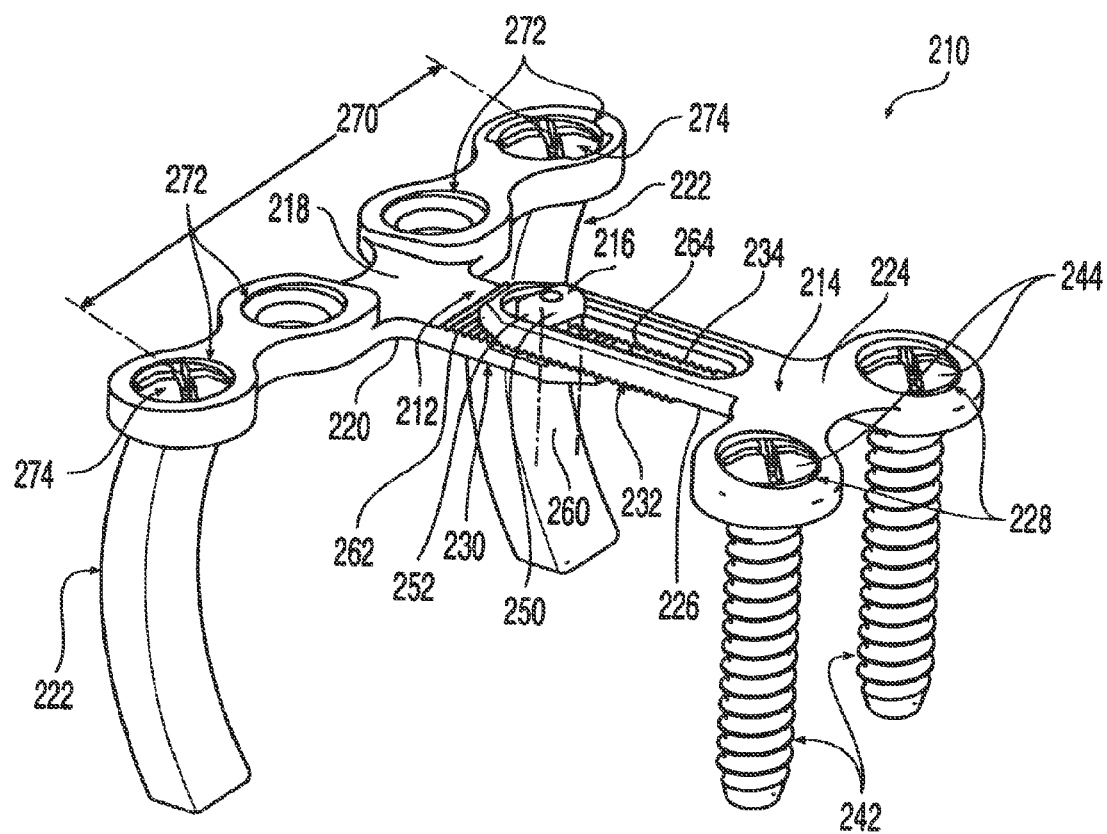
FIG. 16 is a perspective view of the sternum fixation device of FIG. 15, having adjustably spaced-apart hook members.
Figure 17:
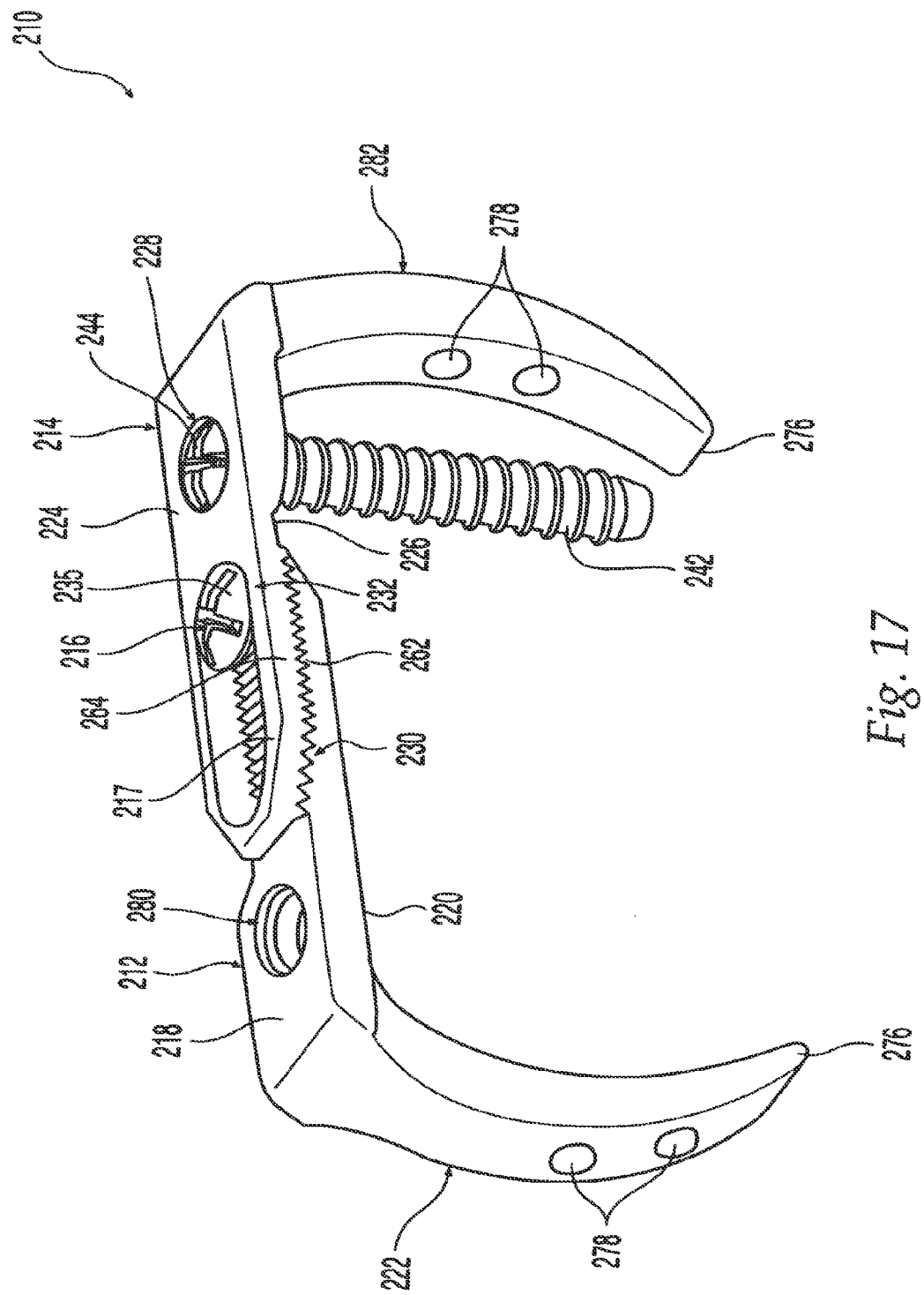
FIG. 17 is a perspective view of the sternum fixation device of FIG. 15, having first and second attachment members including a combination of hooks and threaded fastener holes.

Referring to FIGS. 15-17, a second embodiment of the present invention is shown as sternum fixation device 210. Sternum fixation device 210 includes first and second plates 212, 214 attached to one another by release member 216. First plate 212 includes an upper surface 218 and a sternum-contacting surface 220, and first attachment member 222. As will be discussed in more detail below, first attachment member 222 is a plurality of hooks that are configured and dimensioned to engage the sternum between the intercostal spaces. Second plate 214 includes an upper surface 224 and a sternum-contacting surface 226, and second attachment member 228. Second attachment member 228 is a plurality of holes for receiving a bone fastener or screw 242, which holes are preferably threaded to receive a threaded head 244 of the bone screw 242.

First plate 212 further includes a first joining portion 230 that overlaps with corresponding second joining portion 232 on second plate 214. An elongated slot 234 extends through the second joining portion 232 and is dimensioned to receive release member 216, which is a cam, as shown in FIGS. 15 and 16, or quarter-turn fastener or screw, as shown in FIG. 17. As shown in FIGS. 15 and 16, release member 216 may be a generally rectangular cam that is rotatable between a locking position and a releasing position and has a first dimension 260 that can pass through the slot 234 when it is oriented parallel thereto, but cannot pass through the slot 234 when it is substantially transverse thereto. Thus, when release member 216 is in the locking position, the first dimension 260 is oriented substantially transverse to the elongated slot 234 and locks the first and second plates 212, 214 together. When release member 216 is rotated into the releasing position, the first dimension 260 is in alignment with the elongated slot 234 and allows separation of the first and second plates. FIG. 17 shows release member 216 as a quarter-turn screw having a head 235 and a threaded portion 237 (hidden). Threaded portion 237 passes through elongated slot 234 and engages a threaded bore 236 (hidden) in first joining portion 230, and head 235 engages the upper surface 224 of second joining portion 232 to lock the first and second plates 212, 214 together. According to either configuration of release member 216, cam or quarter-turn screw, the first and second plates 212, 214 may be separated by rotating release member 216 through a predetermined angle preferably of less than 360 degrees, such as, for example, ninety degrees, to free release member 216 from elongated slot 234 and allow the first and second plates 212, 214 to separate. One of ordinary skill in the art will know and appreciate that any number of cam or quarter-turn screw configurations may be used to releasably lock the first and second plates 212, 214 together.

Referring to FIGS. 15-17, first and second joining portions 230, 232 may each have a series of transverse ratchet teeth 262, 264 defined thereon that cooperate to lock first and second plates 212, 214 together. The position of second joining portion 232 may be varied incrementally with respect to first joining portion 230, provided that release member 216 is maintained within the boundaries of elongated slot 234, which position may be locked by the cooperation of transverse ratchet teeth 262, 264, which are pressed together by release member 216. Thus, first and second plates 212, 214 can be locked together at varying distances apart from one another, allowing sternum fixation device 210 to be used with sternums of different sizes.

Figure 18:
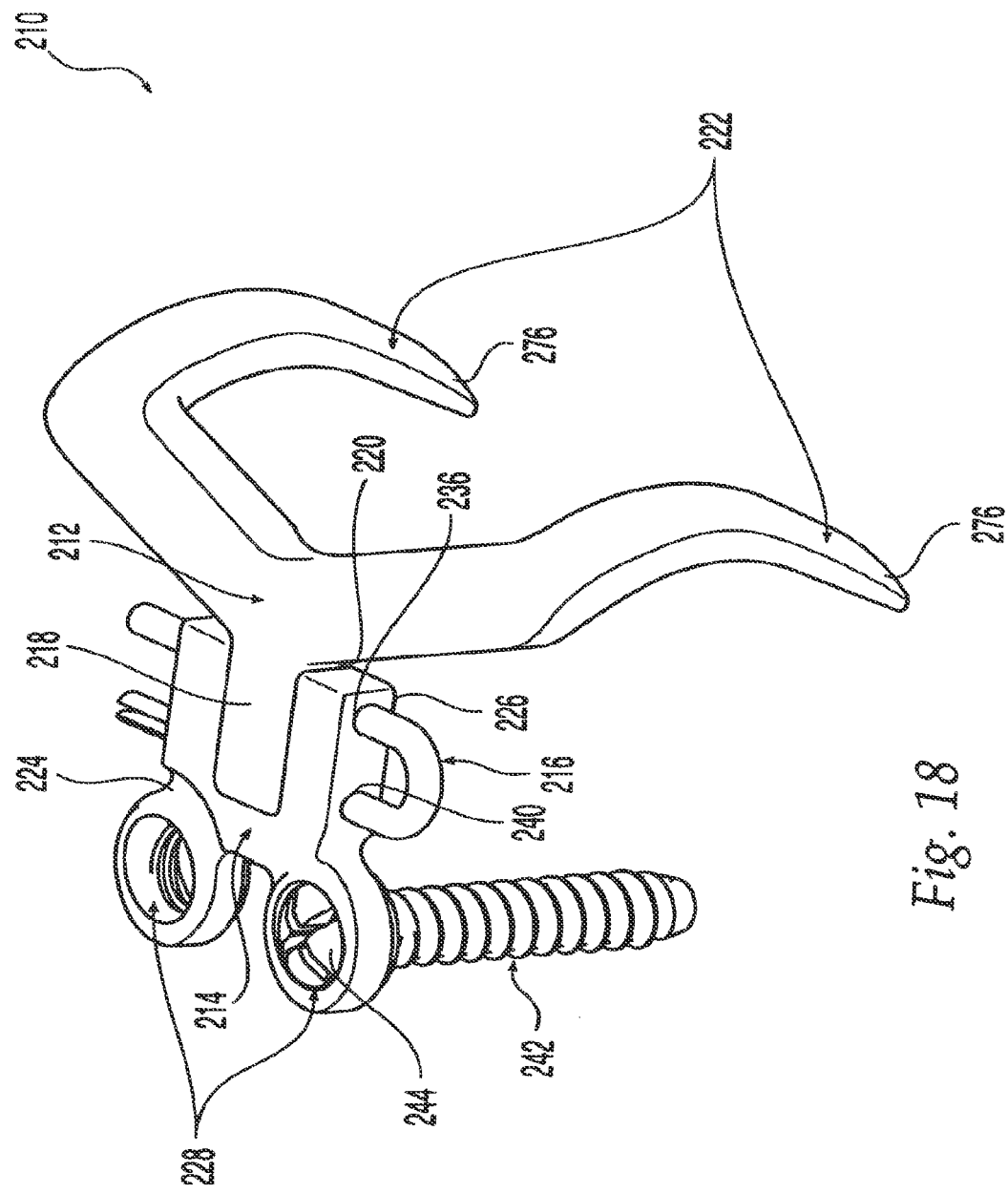
FIG. 18 is a perspective view of the sternum fixation device of FIG. 15, having an alternate embodiment of the release member.

FIG. 18 shows a variation of sternum fixation device 210 where release member 216 is a U-shaped pin that is received in sets of substantially aligned longitudinal bores 234 (hidden), 236 and 238 (hidden), 240 disposed in interdigitated first and second joining portions 230, 232, as described above with respect to sternum fixation device 10. One of ordinary skill in the art will appreciate that all the configurations of the release member 16 and the first and second joining portions 30, 32, as described above with respect to sternum fixation device 10, may also be used with sternum fixation device 210.

Referring back to FIG. 15, first attachment member 222 is shown as a pair of laterally spaced-apart, generally curved hooks for engaging the intercostal spaces of a patient's sternum. First attachment member 222 may have C-shaped, J-shaped, L-shaped, or any other shaped hooks known in the art to be suitable for engaging the intercostal spaces of a sternum. One of ordinary skill in the art will appreciate that first attachment member 222 may have any number of hooks configured for engaging any respective number of intercostal spaces. In addition, first attachment member 222 can be made having various different dimensions, such as the size of the hooks and the lateral spacing therebetween, to accommodate sternums having different sizes and proportions. FIG. 16 shows a variation of first attachment member 222 where the number of hooks and the lateral distance between 270 them is adjustable. First plate 212 has a longitudinal array of mounting apertures 272 defined therein for receiving mounting bolts 274 that secure the hooks to the first plate 212, thus allowing the mounting position of the hooks to be adapted to conform to varying distances between intercostal spaces. Mounting bolts 274 are preferably recessed into mounting apertures 272, for example, by countersinking or counterboring the apertures 272, to reduce the amount of material protruding above upper surface 218. Referring to FIGS. 17 and 18, the first attachment member 222 can have pointed, self-dissecting tip portions 276 that aid in inserting the hooks through soft tissue and muscle that is found in the intercostal spaces. First attachment member 222 can additionally have apertures 278 (shown in FIG. 17) defined therein for receiving pins that may be used to stabilize attachment member 222 in the intercostal space.

While it is apparent that the illustrative embodiments of the invention herein disclosed fulfill the objectives stated above, it will be appreciated that numerous modifications and other embodiments may be devised by those skilled in the art. For example, as shown in FIG. 17, sternum fixation device 210 may further include third attachment member 280, a threaded hole for receiving a threaded head portion 244 of a bone fastener or screw 242, and fourth attachment member 282, an intercostal space hook. One of ordinary skill in the art will appreciate that sternum fixation device 210 may include any number and combination of attachment members, such as hooks and bone screws, and release members, such as pins, U-shaped pins, and cam members. Therefore, it will be understood that the appended claims are intended to cover all such modifications and embodiments which come within the spirit and scope of the present invention.

What is claimed:

1. A sternum fixation device comprising:
   a first plate having an upper surface, an opposed lower surface configured to face a first portion of a sternum, a first joining portion, and at least one first attachment member configured for fixation to the first portion of the sternum, the at least one attachment member including at least one hook and at least one hole, the at least one hole configured to receive a bone screw;
   a second plate having an upper surface, an opposed lower surface configured to face a second portion of the sternum, a second joining portion configured to overlap with the first joining portion of the first plate, and at least one second attachment member configured for fixation to the second portion of the sternum,
   wherein the first and second joining portions carry respective first and second series of teeth configured to intermesh so as to lock the first plate and second plates in an overlapping configuration, the overlapping configuration defined as when the second joining portion of the second plate overlaps the first joining portion of the first plate; and
   a release member configured to rotate between a locking position and a releasing position, wherein when the release member is in the locking position, the first and second series of teeth intermesh so as to releasably secure the first plate to the second plate in the overlapping configuration, and when the release member is in the releasing position the first and second joining portions are moveable with respect to each to other.

2. The sternum fixation device of claim 1, wherein the at least one first attachment member comprises at least one bone screw configured to be inserted in a respective at least one hole, such that the received at least one bone screw is configured for fixation to the first portion of the sternum.

3. The sternum fixation device of claim 1, wherein the at least one first attachment member comprises first and second holes that extend through the upper and lower surfaces, respectively, of the first plate, and the at least one hole of the second attachment member comprises third and fourth holes that extend through the upper and lower surfaces, respectively, of the second plate.

4. The sternum fixation device of claim 3, wherein respective centers of the first and second holes are aligned along a first axis that is disposed on a first side of an intersection of the first and second joining portions when in the overlapping configuration, and respective centers of the third and fourth holes are aligned along a second axis that is disposed on a second side of the intersection that is opposite the first side.

5. The sternum fixation device of claim 4, wherein the first and second axes extend substantially parallel to each other.

6. The sternum fixation device of claim 5, wherein the respective centers of the first and third holes are aligned along a third axis and the respective centers of the second and fourth holes are aligned along a fourth axis, the third and fourth axes spaced from each other and oriented substantially perpendicular to the first and second axes.

7. The sternum fixation device of claim 6, wherein the first and second joining portions are enclosed within a perimeter defined by respective portions of the first, second, third, and fourth axes.

8. The sternum fixation device of claim 6, wherein the at least one hook is at least one first hook, wherein the at least one first attachment member further comprises the at least one first hook such that the at least one first hook is configured to be inserted into an intercostal space of the first portion of the sternum.

9. The sternum fixation device of claim 8, wherein one of the at least one first hook is disposed on a fifth axis that is located substantially equidistantly between the third and fourth axes and extends substantially parallel to the third and fourth axes.

10. The sternum fixation device of claim 6, wherein the at least one hook is disposed on the first side of the intersection such that the first axis is located between the hook and the intersection.

11. The sternum fixation device of claim 8, wherein the at least one second attachment member further comprises at least one second hook configured to be inserted into an intercostal space of the second portion of the sternum.

12. The sternum fixation device of claim 11, wherein the at least one first and second hooks are disposed on a fifth axis that is located substantially equidistantly between the third and fourth axes and extends substantially parallel thereto.

13. The sternum fixation device of claim 12, wherein the at least one first hook is disposed on the first side of the intersection such that the first axis is located between the hook and the intersection and the at least one second hook is disposed on the second side of the intersection such that the second axis is located between the second hook and the intersection.

14. The sternum fixation device of claim 1, wherein the at least one hole of the at least one first attachment member is a first plurality of holes that extend through the upper and lower surfaces, respectively, of the first plate and the at least one second attachment member comprises a second plurality of holes that extend through the upper and lower surfaces, respectively, of the second plate.

15. The sternum fixation device of claim 14, wherein the second joining portion defines at least one bore that extends therethrough along a first direction, the at least one bore being configured to receive at least a portion of the release member.

16. The sternum fixation device of claim 15, wherein respective centers of the first and second plurality of holes are aligned along respective first and second axes that are substantially perpendicular to the first direction.

17. The sternum fixation device of claim 15, wherein respective centers of the first plurality of holes are aligned along a first axis and respective centers of the second plurality of holes are aligned along a second axis, the first and second axes angularly offset with respect to the first direction.

18. The sternum fixation device of claim 1, wherein the first and second joining portions are positioned relative to each other along a first direction in the overlapping configuration, wherein when the release member is in the releasing position, the first and second joining portions are moveable with respect to each other along a second direction that is perpendicular to the first direction.

19. The sternum fixation device of claim 18, wherein the upper surface of the second plate is spaced from the lower surface of the second plate along a first direction the second joining portion includes a slot that is elongate along the second direction that is perpendicular to the first direction.

20. The sternum fixation device of claim 19, wherein the release member is configured to be connected to the first joining portion and positioned in the slot, such that when the release member is in releasing position, the release member is moveable in the slot as the first and second joining portions move with respect to each other along the second direction.

21. The sternum fixation device of claim 20, wherein the at least one first attachment member includes a first plurality of hooks that extend from the first plate and are aligned along a first axis, and the at least one second attachment member includes a second plurality of hooks that extend from the second plate and are aligned along a second axis.

22. The sternum fixation device of claim 21, wherein the first axis is parallel to the second axis.

23. The sternum fixation device of claim 21, wherein when 1) the first and second plates are in the overlapping configuration, and 2) the release member is in the releasing position, the first and second plates are moveable between a first overlapping position and a second overlapping position, the first overlapping position defined as when the at least one first attachment member and the at least one second attachment member are spaced apart with respect to each other a first distance, and the second overlapping position is defined as when the at least one first attachment member and the at least one second attachment member is spaced apart with respect to each other a second distance that is less than the first distance.

24. The sternum fixation device of claim 23, wherein when the first and second plates are in the second overlapping position, the first axis extends through the second joining portion.

25. The sternum fixation device of claim 20, where the at least one hook is at least one first hook, and the at least one hole is at least one first hole, such the at least one first attachment member includes the at least one first hook and at least one first hole, and the at least one second attachment member includes at least one second hook and the at least one second hole.

* * * * *